(12) United States Patent
Wu et al.

(10) Patent No.: US 7,528,263 B2
(45) Date of Patent: May 5, 2009

(54) OXIDATION PROCESS FOR THE PREPARATION OF N-[3-AMINO-1-(CYCLOBUTYLMETHYL)-2,3-DIOXOPROPYL]-3-{N-[(TERT-BUTYLAMINO)CARBONYL]-3-METHYL-L-VALYL}-6,6-DIMETHYL-3-AZABICYCLO[3.1.0]HEXANE-2-CARBOXAMIDE AND RELATED COMPOUNDS

(75) Inventors: George Wu, Basking Ridge, NJ (US); Ji Xie, Edison, NJ (US); Paitoon Rashatasakhon, Piscataway (TH); Frank Xing Chen, Plainsboro, NJ (US); Marc Poirier, Stewartsville, NJ (US); Victoria M. Sprague, North Plainfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 155 days.

(21) Appl. No.: 11/598,528

(22) Filed: Nov. 13, 2006

(65) Prior Publication Data

US 2007/0149459 A1    Jun. 28, 2007

Related U.S. Application Data

(60) Provisional application No. 60/736,542, filed on Nov. 14, 2005.

(51) Int. Cl.
C07D 209/52    (2006.01)

(52) U.S. Cl. .................................... 548/515; 548/452

(58) Field of Classification Search ............. 548/452, 548/515
See application file for complete search history.

(56) References Cited

U.S. PATENT DOCUMENTS

| | | | |
|---|---|---|---|
| 6,992,220 B2 | 1/2006 | Chen | |
| 7,012,066 B2 | 3/2006 | Saksena et al. | |
| 7,309,717 B2 | 12/2007 | Park et al. | |
| 7,326,795 B2* | 2/2008 | Sudhakar et al. | ........... 548/515 |
| 2005/0059684 A1 | 3/2005 | Dolitzsky | |
| 2005/0059800 A1 | 3/2005 | Sudhakar | |
| 2005/0249702 A1 | 11/2005 | Njoroge et al. | |
| 2007/0032433 A1 | 2/2007 | Saksena | |

FOREIGN PATENT DOCUMENTS

WO    WO2004/113294    12/2004
WO    WO2005/085275    9/2005

OTHER PUBLICATIONS

International Search Report, PCT/US2006/043950; mailed May 15, 2007; 4 pages.
Catalano, John G.; et. al.; "Design of small molecule ketoamide-based inhibitors of cathepsin K." Bioorganic & Medicinal Chemistry Letters; Feb. 9, 2004; vol. 14, No. 3; pp. 719-722.
Becker H.G.O; "H0CI (in Form von NaOCI „,", Journal Fur Praktische Chemie . . . , vol. 337; 1995; pp. 690-691.

* cited by examiner

*Primary Examiner*—Golam M Shameem
(74) *Attorney, Agent, or Firm*—Patent Practitioners of Schering Corporation

(57) ABSTRACT

The present application relates to a process for preparing a compound of formula I:

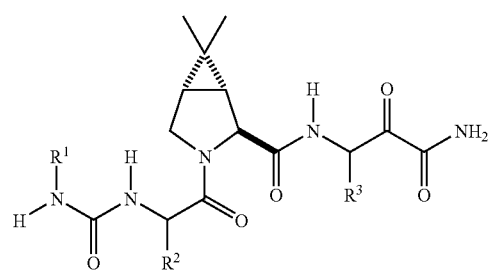

wherein
$R^1$ is alkyl;
$R^2$ is alkyl; and
$R^3$ is optionally substituted cycloalklylalkyl
which comprises oxidizing a compound of the formula

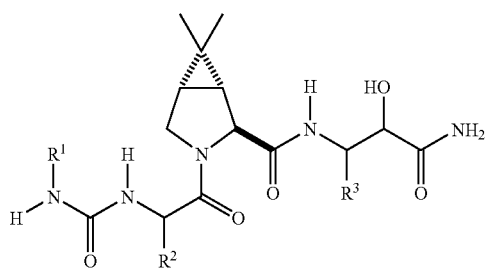

wherein $R^1$, $R^2$ and $R^3$ are defined above
to yield a compound of formula I.

32 Claims, No Drawings

OXIDATION PROCESS FOR THE PREPARATION OF N-[3-AMINO-1-(CYCLOBUTYLMETHYL)-2,3-DIOXOPROPYL]-3-{N-[(TERT-BUTYLAMINO)CARBONYL]-3-METHYL-L-VALYL}-6,6-DIMETHYL-3-AZABICYCLO[3.1.0]HEXANE-2-CARBOXAMIDE AND RELATED COMPOUNDS

CROSS REFERENCE TO PRIORITY APPLICATION

This application claims the benefit of priority from U.S. provisional patent application Ser. No. 60/736,542 filed Nov. 14, 2005

FIELD OF THE INVENTION

This invention relates to a novel oxidation process for the preparation of N-[3-amino-1-(cyclobutylmethyl)-2,3-dioxopropyl]-3-{N-[(tert-butylamino)carbonyl]-3-methyl-L-valyl}-6,6-dimethyl-3-azabicyclo[3.1.0]hexane-2-carboxamide compounds having the following structure of formula A:

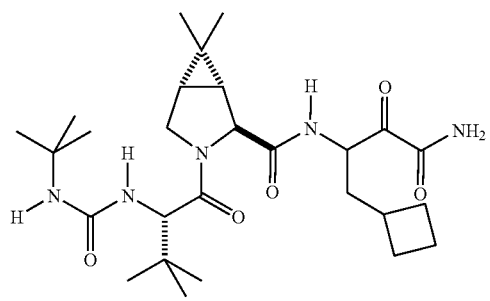

and other related compounds, including all stereoisomers.

BACKGROUND OF THE INVENTION (1R,2S,5S)-N-[3-amino-1-(cyclobutylmethyl)-2,3-dioxopropyl]-3-{N-[(tert-butylamino)carbonyl]-3-methyl-L-valyl}-6,6-dimethyl-3-azabicyclo[3.1.0]hexane-2-carboxamide is disclosed in U.S. Publication No. 2003/0216324 A1 (now U.S. Pat. No. 7,012,066), and U.S. application Ser. No. 10/052,386, (now U.S. Pat. No. 7,244,271), which was filed Jan. 18, 2002, Ser. No. 10/867,600, (now U.S. Pat. No. 7,326,795), 10/867,601, (now U.S. Pat. No. 6,992,220), and U.S. No. 10/867,602 (now U.S. Pat. No. 7,309,717) which were all filed on Jun. 15, 2004, all of which are each incorporated herein by reference.

The compound of formula A is a hepatitis C virus ("HCV") protease inhibitor, useful for treating hepatitis C and related disorders. Specifically, the compound of formula A is an inhibitor of the HCV NS3/NS4a serine protease.

There remains a need for compounds useful in the treatment or prevention or amelioration of one or more symptoms of hepatitis C.

In view of the importance of hepatitis C virus ("HCV") protease inhibitors, new, novel methods of making such antagonists are always of interest.

SUMMARY OF THE INVENTION

In an aspect, the present application relates to process of making a compound of formula I:

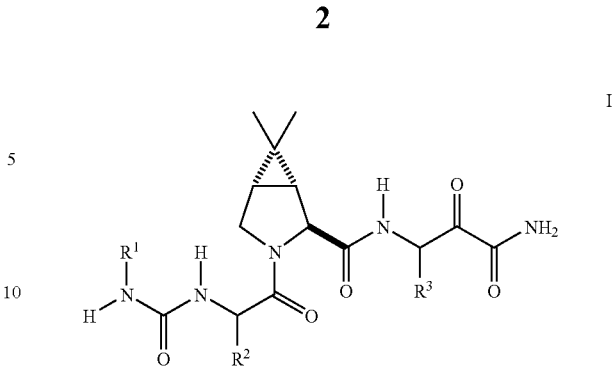

wherein
R$^1$ is alkyl;
R$^2$ is alkyl; and
R$^3$ is optionally substituted cycloalklylalkyl including all stereoisomers, rotomers, enantiomers and diasteromers by oxidizing a compound of formula I

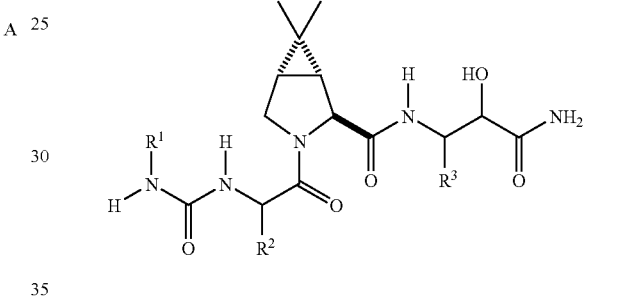

The inventive oxidation process to make compounds of formula I has several advantages, including the provision of a simple one step oxidation procedure to form the compound of formula I in high yield.

DESCRIPTION OF THE INVENTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl, groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylalkyl" means a cycloalkyl-alkyl group in which the cycloalkyl and alkyl groups are as previously described. The cycloalkyl portion may be optionally substituted with one or more "ring system substituents." The alkyl portion may be substituted with one or more alkyl substituents as defined above.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means R—C(O)— group wherein R is, for example, hydrogen or any of the groups described in the definitions listed above. Examples of such groups include H—C(O)—, alkyl-C(O)—, alkenyl-C(O)—, alkynyl-C(O)—, cycloalkyl-C(O)—, cycloalkenyl-C(O)—, or cycloalkynyl-C(O)— group. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-$S(O_2)$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

The disclosure provides methods for preparing compounds of formula I, including various isomers and pharmaceutically acceptable salts. It will be appreciated that the present description can be modified to provide variously desired isomers and salts, which are within the scope of the invention.

One embodiment of the invention involves a process of making a compound of formula IA comprising:

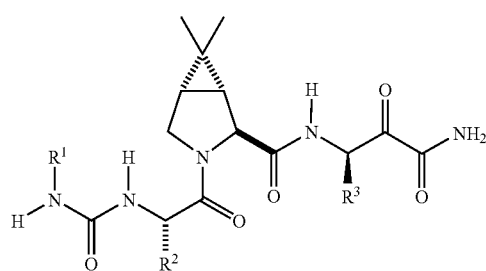

wherein R¹, R² and R³ are defined above which comprises oxidizing a compound of formula IIA

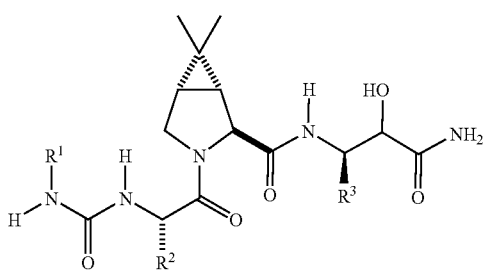

to yield a compound of formula IA.

Another embodiment of the invention is a process of making a compound of formula IB

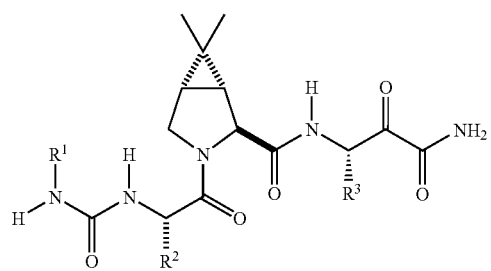

wherein R¹, R² and R³ are defined above, which comprises oxidizing a compound of formula IIB

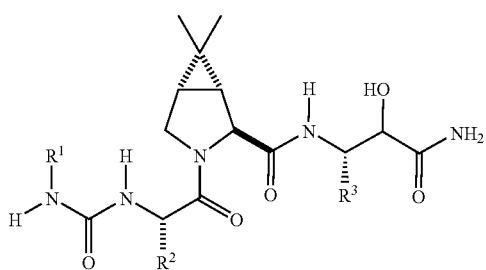

to yield a compound of formula IIB.

Another embodiment of the invention is a process for making a compound of formula IC

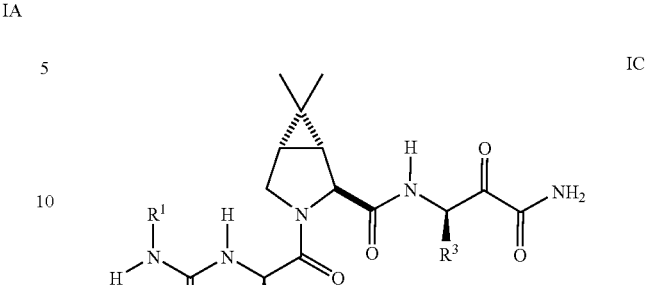

wherein R¹, R² and R³ are defined above which comprises oxidizing a compound of formula IIC

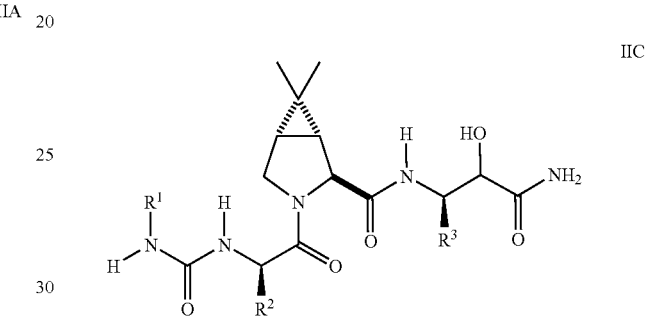

to yield a compound of formula IC.

Another embodiment of the invention is a process of making a compound of formula ID,

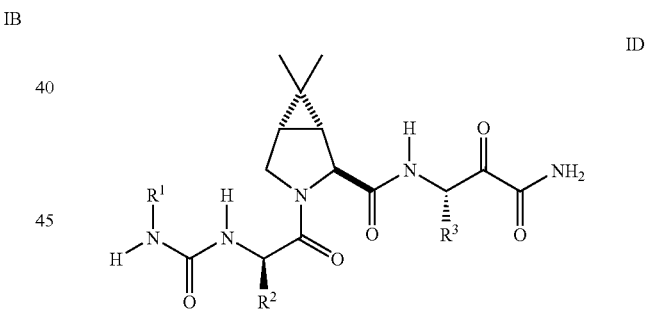

wherein R¹, R² and R³ are defined above which comprises oxidizing a compound of formula IID

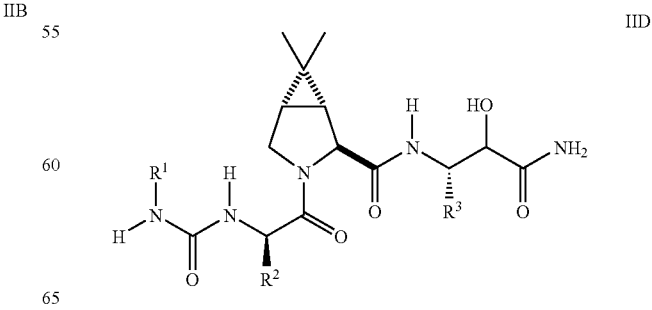

to yield a compound of formula ID.

Compounds of formula II can be prepared according to processes found in the prior art, for example, those found in US Publication Nos. US 2003/0216325 A1 and US 2004/0254117 A9, both herein incorporated by reference. It will be appreciated that the processes disclosed therein can be modified without undue experimentation to prepare specifically desired starting materials.

Non-limiting examples of an oxidation agent that oxidizes compounds of formula II to those of formula I include Na(ClO), Ca(OCl)$_2$, and NaBrO$_3$. The oxidation agent can be used generally in an amount ranging from about 0 to 4, and for example from about 1 to about 2 equivalents with respect to a compound of formula II.

In some embodiments of the invention, it is preferred for the process to include the use of a catalyst and optionally a co-catalyst. Non-limiting examples of a catalyst that may be used in the inventive process include tetramethylpiperidinyloxy (TEMPO), 2-methoxyTEMPO, and 4-aminoTEMPO. The catalyst can be used generally in an amount ranging from about 0.1 to about 3, and for example from about 1 to about 2 equivalents with respect to a compound of formula II.

In some embodiments of the invention, it is preferred to have at least one co-catalyst is present in the reaction mixture. Non-limiting examples of suitable co-catalysts include metal acetates, for example, sodium, lithium or potassium acetate, metal halides, for example, sodium bromide, potassium bromide or sodium iodide. The co-catalyst can be used in amounts ranging from 0 to saturation, more preferably from 0 to about 2 equivalents or from about 0.5 to about 1.5 equivalents and most preferably about 0.9 equivalents, all with respect to a compound of formula II. When present, preferably 1 or 2 co-catalysts are present in the process.

Another embodiment of the inventive process includes the presence of an acid. Non-limiting examples of acids include acetic acid or a halogenated acetic acid, such as ClCH$_2$COOH, Cl$_2$CHCOOH, Cl$_3$CCOOH, and CF$_3$COOH. The acid can be used generally in an amount ranging from about 0.1 to about 3, and for example from about 1 to about 2 equivalents with respect to a compound of formula II.

Non-limiting examples of solvents include esters, ethers, water or mixtures thereof. A biphasic solvent system can be used, for example a system comprising t-butyl methylether and water. Preferably the solvent is methyl tertiary-butyl ether (MTBE).

The oxidation can be carried out at a temperature ranging from about 0° C. to about 80° C., for example from about 10° C. to about 50° C., and as a further example from about 15° C. to about 30° C.

In some embodiments of the present invention, it is preferred to carry out the oxidation by contacting a compound selected from a compound of Formula IIA, IIB, IIC and IID with an oxidation agent, a catalyst, one or two co-catalysts, and an acid in a solvent or solvent mixture.

In some embodiments of the present invention process employing a catalyst, it is preferred to include additionally, after the oxidation step, a step in which the catalyst is removed by adding to the reaction mixture a catalyst removing reagent. Examples of catalyst removing reagents include, but are not limited to, ascorbic acid and one or more of a mineral acid, for example, HCl and HBr, and mixtures of two or more thereof. The catalyst removing reagent can generally be used in an amount ranging from 0 to about 4 equivalents, more preferably from about 0.1 to about 3 equivalent or from about 1 to about 3 equivalents.

In some embodiments employing a mineral acid as a catalyst removing reagent, it is preferred to use a mineral acid concentration of from about 1N to about 5N. In some embodiments using HCl as a catalyst removing reagent it is preferred to use a concentration of HCl which is about 3.5 N. In some embodiments using a mineral acid as a catalyst removing reagent it is preferred to use the mineral acid in an amount of from about 1 to about 10 times the amount of catalyst employed.

Preferred groups for $R^1$ and $R^2$ include methyl, ethyl, n-propyl, i-propyl, n-butyl, sec-butyl, iso-butyl or tert-butyl. Especially preferred are compounds wherein $R^1$ and $R^2$ are both tert-butyl.

Preferred groups for $R^4$ include groups of the formula —(CH$_2$)$_n$—$R^4$, wherein $R^4$ is a moiety selected from the group consisting of cyclopropyl, cyclobutyl, cyclopentyl and cyclohexyl and n is an integer from 1-10, more preferably from 1-5. Especially preferred compounds are those wherein n is 1 and $R^4$ is cyclobutyl.

Representative illustrative procedures are outlined in the following reaction schemes. It is to be understood that while the following illustrative schemes describe the preparation of a few representative inventive compounds, suitable substitution can result in the formation of the desired compounds based on such substitution. Such variations are contemplated to be within the scope of the invention.

The following non-limiting EXAMPLE is provided in order to further illustrate the present invention. It will be apparent to those skilled in the art that many modifications, variations and alterations to the present disclosure, both to materials, methods and reaction conditions, can be practiced. All such modifications, variations and alterations are intended to be within the spirit and scope of the present invention.

EXAMPLES

Preparation of (1R,2S,5S)-N-[3-amino-1-(cyclobutylmethyl)-2,3-dioxopropyl]-3-{N-[(tert-butylamino)carbonyl]-3-methyl-L-valyl}-6,6-dimethyl-3-azabicyclo-[3.1.0]hexane-2-carboxamide(the Compound of Structure 2 in Scheme A, Below)

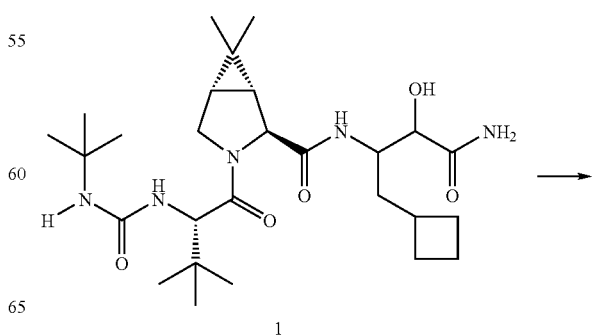

-continued

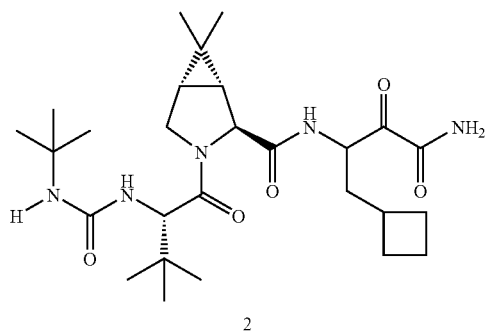

2

Unless otherwise stated, the following abbreviations have the stated meanings in the Examples below:
g=grams
mL=milliliters
eq=equivalents
mmols=millimols
DMF=dimethylformamide
NaOAc=sodium acetate
TEMPO=2,2,6,6-tetramethyl-1-piperidinyloxy free radical (available from Aldrich and used as received)
MTBE=methyl tert-butyl ether
NaOCl=sodium hypochlorite
Equiv=equivalent(s)

Unless otherwise noted all solvents are articles of commerce and all reagents were used as received.

Example 1

Preparation of Compound 2 Using Aqueous Acetic Acid in the Reaction Mixture

Into a 1 L, three necked flask is placed KBr (10 g, 84 mmol), NaOAc (10 g, 122 mmol), Compound 1 (50 g, 96 mmol), and TEMPO (15 g, 96 mmol), followed by 500 mL of MTBE. The reaction mixture is stirred at 350-400 rpm and the temperature is maintained at a temperature of from 10° C. to 20° C. Acetic acid (50 mL, 874 mmol), and water (5 mL) are added to the reaction mixture and the two phase mixture is agitated for 15 minutes. Continuously, over a two hour period, to the reaction mixture is added 158 mL of a 0.82 M solution of NaOCl (130 mmol). When all of the NaOCl solution is added, the reaction mixture is stirred for an additional 3 hours while maintaining the temperature. Water (50 mL) is added. The layers are separated and the organic layer is washed twice with water (2×250 mL). A solution of ascorbic acid, which is prepared from 50 g of sodium ascorbate, 200 mL of water, and 50 mL of 4N HCl, is added to the organic layer and the mixture is stirred for about 1 hour. After the layers are separated, the organic layer is washed twice with water (2×250 mL). The organic layer is concentrated by distilling off solvent at low temperature (0-5° C.) until the total volume is about 350 mL. The concentrated organic layer is added drop-wise over 30 minutes into a 3 L flask containing 2 L of n-heptane at about 0° C. providing a white precipitate. The white precipitate is collected by filtration, washed with n-heptane (400 mL) and dried in a vacuum oven (2 hr at 25° C., 8 hr at 35°, and 8° C. at 45° C.). The product is obtained as a white powder (typically 94-96% yield). $^1$H NMR, δ 0.84 (d, J=2.3 Hz, 3H), 0.90-1.02 (m, 9H), 0.99 (d, J=4.0 Hz, 3H), 1.24 (s, 9H), 1.40-1.86 (m, 7H), 1.90-2.10 (m, 3H), 2.25-2.40 (m, 1H), 3.75 (dd, J=5.3 and 10.4 Hz, 1H), 4.10 (dd, J=6.8 and 10.4 Hz, 1H), 4.4 (dd, J=3.0 and 5.3 Hz, 2H), 5.17 (dddd, J=4.6, 8.1, 8.1, and 10.4 Hz, 1H), 5.3 (br s, 2H), 6.71 (d, J=14.7 Hz, 1H), 6.90 (dd, J=2.3 and 19.0 Hz, 1H), and 7.34 (dd, J=7.1 and 20.2 Hz, 1H).

Example 2

Preparation of Compound 2 Using Glacial Acetic Acid in the Reaction Mixture

Into a 2 L, three necked flask was charged KBr (20 g, 168 mmol), NaOAc (20 g, 243 mmol), Compound 1 (100 g, 192 mmol), and TEMPO (30 g, 192 mmol), followed by 800 mL of MTBE. The reaction mixture was stirred at 350-400 rpm while the temperature of the reaction mixture was maintained at a temperature of from 10° C. to 20° C. Acetic acid (70 mL, 1223 mmol, used as received), was added and the mixture was agitated for 15 minutes additional. Continuously, over a two hour period, 315 ml of a 0.73M solution of NaOCl (230 mmol) was added to the reaction mixture. When all of the NaOCl solution had been added, agitation was continued for an additional 3 hours. Water (100 mL) was added to the reaction mixture at the end of 3 hours. The layers were separated and the organic layer was washed once with water (500 mL). A solution of ascorbic acid, which was prepared from 100 g of sodium ascorbate, 456 mL of water, and 44 mL of 36% HCl, was added to the organic layer and the mixture was stirred for about 2 hours. The layers were separated and then a solution of 3.5N HCL was added and stirred about 30 minutes. After the layers were separated, the organic layer was washed three times with water (3×500 mL). This organic layer was then added drop-wise over 30 minutes into a 5 L flask containing 3 L of n-heptane at about −10 to about 0° C. The white precipitate was filtered, washed with n-heptane (600 mL) and dried in a vacuum oven (2 hr at 25° C., 8 hr at 35°, and 8° C. at 45° C.). The product was obtained as a white powder (93% yield). $^1$H NMR, δ 0.84 (d, J=2.3 Hz, 3H), 0.90-1.02 (m, 9H), 0.99 (d, J=4.0 Hz, 3H), 1.24 (s, 9H), 1.40-1.86 (m, 7H), 1.90-2.10 (m, 3H), 2.25-2.40 (m, 1H), 3.75 (dd, J=5.3 and 10.4 Hz, 1H), 4.10 (dd, J=6.8 nd 10.4 Hz, 1H), 4.4 (dd, J=3.0 and 5.3 Hz, 2H), 5.17 (dddd, J=4.6, 8.1, 8.1, and 10.4 Hz, 1H), 5.3 (br s, 2H), 6.71 (d, J=14.7 Hz, 1H), 6.90 (dd, J=2.3 and 19.0 Hz, 1H), and 7.34 (dd, J=7.1 and 20.2 Hz, 1H).

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A process for preparing a compound of formula I:

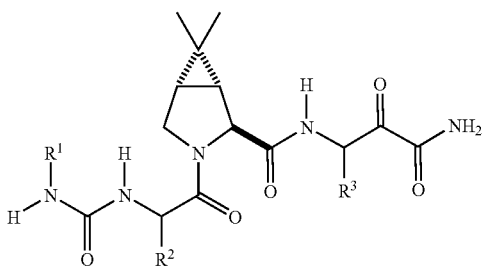

wherein
R¹ is alkyl;
R² is alkyl; and
R³ is optionally substituted cycloalklylalkyl
which comprises oxidizing the compound of Formula II, Formula II

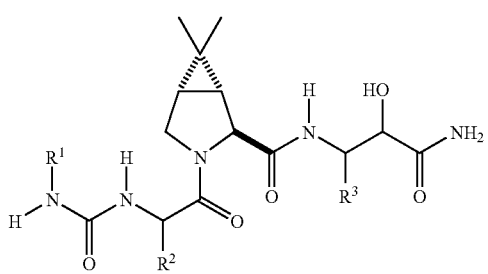

wherein R¹, R² and R³ are defined above
with an oxidizing agent selected from the group consisting of NaClO, Ca(OCl)₂, and NaBrO₃ to yield a compound of formula I.

2. The process of claim 1, wherein from about 1 to about 2 equivalents of the oxidizing reagent is used.

3. The process of claim 1, wherein said oxidation reaction additionally employs a catalyst.

4. The process of claim 3, wherein the catalyst is present in the reaction in an amount of from about 0.1 to about 3 equivalents based on the compound of Formula II.

5. The process of claim 3, wherein the catalyst is selected from the group consisting of TEMPO, 4-methoxyIEMPO, and 4-aminoTEMPO.

6. The process of claim 3, wherein said oxidation reaction additionally employs a co-catalyst.

7. The process of claim 6, wherein the co-catalyst is potassium bromide or sodium bromide.

8. The process of claim 6, which comprises a second co-catalyst.

9. The process of claim 6, wherein the co-catalyst is potassium acetate or sodium acetate.

10. The process of claim 9, wherein the amount of co-catalyst is from about 0.1 to about 3 equivalents.

11. The process of claim 1, wherein said oxidation reaction additionally employs an acid.

12. The process of claim 11, wherein the amount of acid ranges from about 0.1 to about 3 equivalents.

13. The process of claim 11, wherein the acid is selected from the group consisting of acetic acid, ClCH₂COOH, Cl₂CHCOOH, Cl₃CCOOH, and CF₃COOH.

14. The process of claim 1, wherein the oxidation reaction temperature ranges from about 0° C. to about 80° C.

15. The process of claim 1, wherein the reaction temperature ranges from about 10° C. to about 50° C.

16. The process according to claim 7 wherein the oxidizing agent is NaOCl, the catalyst is TEMPO and the co-catalyst is KBr.

17. The process of claim 1, wherein said oxidation reaction temperature ranges from about 15° C. to about 30° C.

18. The process of claim 16, wherein R¹ and R² are tert-butyl and R³ is cyclobutylmethyl.

19. The process of claim 3, which further comprises the step of adding a catalyst removing reagent following the oxidation reaction step.

20. The process of claim 19, wherein the catalyst removing reagent is selected from the group consisting of acorbic acid, a mineral acid, and a mixture thereof.

21. The process of claim 20, wherein the catalyst removing reagent is ascorbic acid, and is added in an amount from about 0.1 to about 3 equivalents.

22. The process according to claim 19, wherein the catalyst removing reagent is HCl at a concentration from about 3N to about 5N and is added in an amount of from about 1 to about 10 times by volume based on the weight of a compound of formula II.

23. A process preparing a compound of formula IA

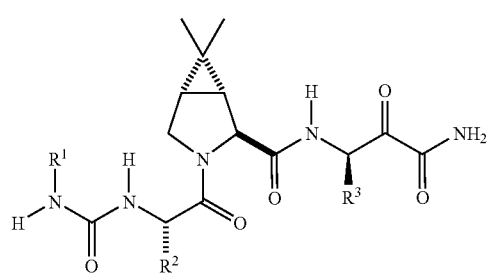

wherein
R¹ is alkyl;
R² is alkyl; and
R³ is optionally substituted cycloalklylalkyl
which comprises oxidizing the compound of Formula IIA

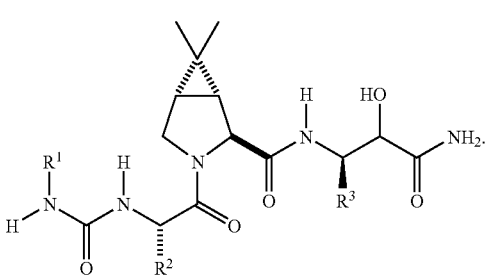

wherein R¹, R² and R³ are defined above,
with an oxidizing agent selected from the group consisting of NaClO, Ca(OCl)₂, and NaBrO₃ to yield a compound of formula IA.

24. The process according to claim 23, wherein R¹ and R² are tert-butyl and R³ is cyclobutylalkyl.

25. A process for the preparation of a compound of formula IB

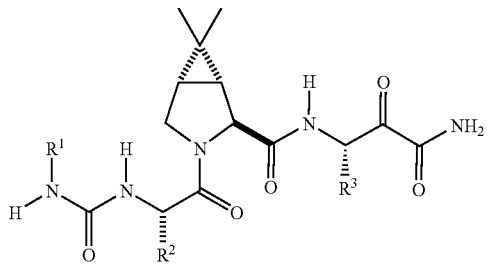

wherein
R$^1$ is alkyl;
R$^2$ is alkyl; and
R$^3$ optionally substituted cycloalklylalkyl
which comprises oxidizing the compound of Formula IIB

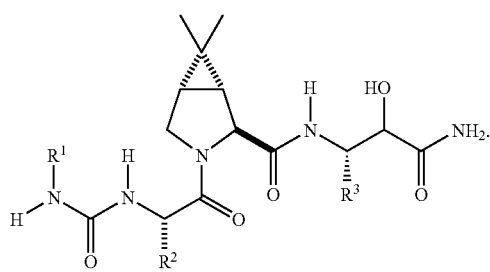

wherein R$^1$, R$^2$ and R$^3$ are defined above,
with an oxidizing agent selected from the group consisting of NaClO, Ca(OCl)$_2$, and NaBrO$_3$ to yield a compound of formula IIB.

26. The process according to claim 25, wherein R$^1$ and R$^2$ are tert-butyl and R$^3$ is cyclobutylalkyl.

27. A process for the preparation of a compound of formula IC

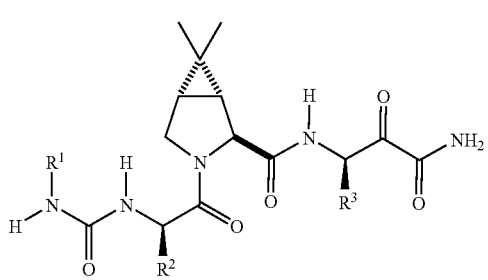

wherein
R$^1$ is alkyl;
R$^2$ is alkyl; and
R$^3$ is optionally substituted cycloalklylalkyl,
which comprises oxidizing the compound of Formula IIC

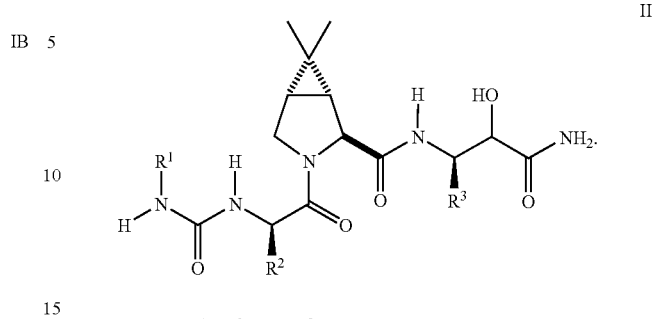

wherein R$^1$, R$^2$ and R$^3$ are defined above
with an oxidizing agent selected from the group consisting of NaClO, Ca(OCl)$_2$, and NaBrO$_3$ to yield a compound of formula IC.

28. The process according to claim 27, wherein R$^1$ and R$^2$ are tert-butyl and R$^3$ is cyclobutylalkyl.

29. A process for the preparation of a compound of formula ID comprising:

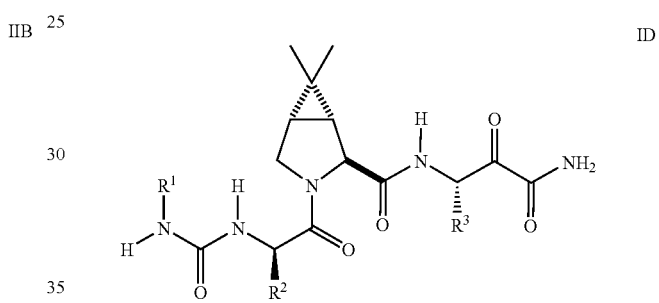

wherein
R$^1$ is alkyl;
R$^2$ is alkyl; and
R$^3$ is optionally substituted cycloalklylalkyl
which comprises oxidizing the compound of Formula IID

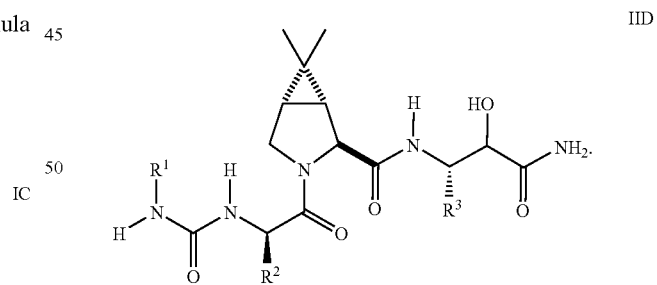

wherein R$^1$, R$^2$ and R$^3$ are defined above,
with an oxidizing agent selected from the group consisting of NaClO, Ca(OCl)$_2$, and NaBrO$_3$ to yield a compound of formula ID.

30. The process according to claim 29, wherein R$^1$ and R$^2$ are tert-butyl and R$^3$ is cyclobutylalkyl.

31. The process of claim 13, wherein the acid selected is acetic acid.

32. The process of claim 31, wherein the water is added to the acetic acid.

* * * * *

UNITED STATES PATENT AND TRADEMARK OFFICE
CERTIFICATE OF CORRECTION

| | | |
|---|---|---|
| PATENT NO. | : 7,528,263 B2 | Page 1 of 1 |
| APPLICATION NO. | : 11/598528 | |
| DATED | : May 5, 2009 | |
| INVENTOR(S) | : George Wu et al. | |

It is certified that error appears in the above-identified patent and that said Letters Patent is hereby corrected as shown below:

Title Page item 75, in the Inventors:

Please change the residence of Inventor Paitoon Rashatasakhon from "Piscataway" to:

-- Samutsakhon, Thailand --

In the Claims:

Claim 5, col. 13, line 49, please correct "4-methoxyIEMPO" to:

-- 4-methoxyTEMPO --

Claim 20, col. 14, line 16, please correct "acorbic" to:

-- ascorbic --

Signed and Sealed this

Twenty-fourth Day of November, 2009

David J. Kappos
*Director of the United States Patent and Trademark Office*